(12) United States Patent
Federoff et al.

(10) Patent No.: US 10,900,977 B2
(45) Date of Patent: Jan. 26, 2021

(54) PROTEIN BIOMARKERS FOR MEMORY LOSS

(71) Applicants: Georgetown University, Washington, DC (US); University of Rochester, Rochester, NY (US)

(72) Inventors: Howard J. Federoff, Bethesda, MD (US); Massimo S. Fiandaca, Millersville, MD (US); Amrita K. Cheema, Potomac, MD (US); Mark E. Mapstone, Pittsford, NY (US); Xiaogang Zhong, College Park, MD (US)

(73) Assignees: Georgetown University, Washington, DC (US); University of Rochester, Rochester, NY (US)

( * ) Notice: Subject to any disclaimer, the term of this patent is extended or adjusted under 35 U.S.C. 154(b) by 0 days.

(21) Appl. No.: 15/768,798

(22) PCT Filed: Oct. 17, 2016

(86) PCT No.: PCT/US2016/057295
§ 371 (c)(1),
(2) Date: Apr. 16, 2018

(87) PCT Pub. No.: WO2017/066739
PCT Pub. Date: Apr. 20, 2017

(65) Prior Publication Data
US 2018/0306811 A1 Oct. 25, 2018

Related U.S. Application Data

(60) Provisional application No. 62/242,461, filed on Oct. 16, 2015.

(51) Int. Cl.
*A61K 38/00* (2006.01)
*C12Q 1/68* (2018.01)
*G01N 33/567* (2006.01)
*G01N 33/68* (2006.01)
*G16B 20/00* (2019.01)
*G16H 50/30* (2018.01)
*G16H 50/20* (2018.01)

(52) U.S. Cl.
CPC ......... *G01N 33/6896* (2013.01); *G16B 20/00* (2019.02); *G16H 50/20* (2018.01); *G16H 50/30* (2018.01); *G01N 2570/00* (2013.01); *G01N 2800/2814* (2013.01); *G01N 2800/60* (2013.01)

(58) Field of Classification Search
None
See application file for complete search history.

(56) References Cited

U.S. PATENT DOCUMENTS

2012/0178637 A1 7/2012 Devanarayan et al.
2014/0200151 A1 7/2014 Bahn et al.
2014/0323338 A1 10/2014 Rai et al.

FOREIGN PATENT DOCUMENTS

WO  WO 98-40748 A1  9/1998

OTHER PUBLICATIONS

Hu et al., "Comparative Proteomic Analysis of Intra- and Interindividual Variation in Human Cerebrospinal Fluid," Molecular & Cellular Proteomics, vol. 4, No. 12, pp. 2000-2009 (2005).
International Search Report and Written Opinion issued in corresponding International Application No. PCT/US2016/057295 dated Jan. 11, 2017.

*Primary Examiner* — Olga N Chernyshev
(74) *Attorney, Agent, or Firm* — Grimes & Yvon LLP (57) ABSTRACT

The present invention relates to methods of determining if a subject has an increased risk of suffering from memory impairment. The methods comprise analyzing at least one plasma sample from the subject to determine a value of the subject's proteomic profile and comparing the value of the subject's proteomic profile with the value of a normal proteomic profile. A change in the value of the subject's proteomic profile, over normal values is indicative that the subject has an increased risk of suffering from memory impairment compared to a normal individual.

3 Claims, 3 Drawing Sheets

PROTEIN BIOMARKERS FOR MEMORY LOSS

STATEMENT REGARDING FEDERALLY SPONSORED RESEARCH OR DEVELOPMENT

This invention was made with government support under grant number R01 AG030753 awarded by the National Institutes of Health and under contract number W81XWH-09-1-0107 awarded by the Department of Defense. The government has certain rights in the invention.

BACKGROUND OF THE INVENTION

Field of the Invention

The present invention relates to methods of determining if a subject has an increased risk of suffering from memory impairment. The methods comprise analyzing at least one plasma sample from the subject to determine a value of the subject's protemic profile and comparing the value of the subject's proteomic profile with the value of a normal proteomic profile. A change in the value of the subject's proteomic profile, over normal values is indicative that the subject has an increased risk of suffering from memory impairment compared to a normal individual.

Background of the Invention

Alzheimer's disease (AD) is a neurodegenerative disorder characterized by a progressive dementia that insidiously and inexorably robs older adults of their memory and other cognitive abilities. The prevalence of AD is expected to double every 20 years from 35.6 million individuals worldwide in 2010 to 115 million affected individuals by 2050. There is no cure and current therapies are unable to slow the progression of the disease.

Early detection of the at-risk population (preclinical), or those in the initial symptomatic stages (prodromal, or mild cognitive impairment, MCI) of AD, may present opportunities for more successful therapeutic intervention, or even disease prevention by interdicting the neuropathological cascade that is ultimately characterized by the deposition of extracellular β-amyloid (Aβ) and accumulation of intracellular fibrils of hyperphosphorylated microtubule associated protein tau (MAPT or tau) within the brain. Biomarkers for early disease, including cerebrospinal fluid (CSF) tau and Aβ levels, structural and functional magnetic resonance imaging (MRI), and the recent use of brain positron emission tomography (PET) amyloid imaging, are of limited use as widespread screening tools since they provide diagnostic options that are either invasive (i.e., require lumbar puncture), time-consuming (i.e., several hours in a scanner for most comprehensive imaging protocols), expensive, or have been primarily validated in comparisons between normal subjects and those with the disease. No current blood-based biomarkers can detect incipient dementia with the required sensitivity and specificity during the preclinical stages. Continued interest in blood-based biomarkers remains because these specimens are obtained using minimally invasive, rapid, and relatively inexpensive methods. With recent technological advances in 'omics' technologies and systems biology analytic approaches, the comprehensive bioinformatic analyses of blood-based biomarkers may not only yield improved accuracy in predicting those at risk, but may also provide new insights into the underlying mechanisms and pathobiological networks involved in AD and possibly herald the development of new therapeutic strategies.

The preclinical interval resulting in MCI or AD is known to be variable, multifactorial, and extends for at least 7-10 years prior to the emergence of clinical signs (prodromal or manifest disease). In the absence of accurate and easily obtained biomarkers, multimodal neurocognitive testing remains the most accurate, standardized, and widely used pre-mortem screening method to determine the presence or absence of clinical MCI or AD. The utility of strict cognitive assessment for preclinical stages of MCI or AD is limited, however, as this approach is not only time-consuming but is expected, by definition, to be normal in preclinical subjects. Neuropsychological testing is able to quantitatively delineate specific brain alterations from normal, such as memory, attention, language, visuoperceptual, and executive functions, which are typically not affected in individuals during the preclinical stages. Thus, information obtained from multiple diagnostic studies will probably be most useful in defining the MCI/AD preclinical stages, including neuropsychological testing and some form(s) of biomarker(s). While CSF and neuroimaging have been used to define preclinical MCI/AD to date, their clinical utility as screening tools for asymptomatic individuals is not established.

SUMMARY OF THE INVENTION

The present invention relates to methods of determining if a subject has an increased risk of suffering from memory impairment. The methods comprise analyzing at least one plasma sample from the subject to determine a value of the subject's proteomic profile and comparing the value of the subject's proteomic profile with the value of a normal proteomic profile. A change in the value of the subject's proteomic profile, over normal values is indicative that the subject has an increased risk of suffering from memory impairment compared to a normal individual.

BRIEF DESCRIPTION OF THE DRAWINGS

FIG. 2 depicts the Plasma Proteomics Index (PPI) for the proteomic data. PPI is a graphical representation of the collapsed data from the 48 protein panels. Initially, the data from the 48 proteins for NC and $C_{pre}$ is used to develop logistic regression coefficients for the individual protein analytes and reduced to a LOGIT score. The combined LOGIT values are then reflected onto a 0-100 scale, providing normal ranges from the data (and variability) for the NC and $C_{pre}$ values. Due to the high ROC AUC values, there is perfect separation between the NC and $C_{pre}$ groups on the PPI, with no overlap between the two groups. This allows the development of accuracy values on the right y axis. Risk Index Values above 100% accuracy reflect absolute risk of phenoconversion from $C_{pre}$ to $C_{post}$. All $C_{pre}$ values are above the 100% confidence line.

DETAILED DESCRIPTION OF THE INVENTION

Figure 1:
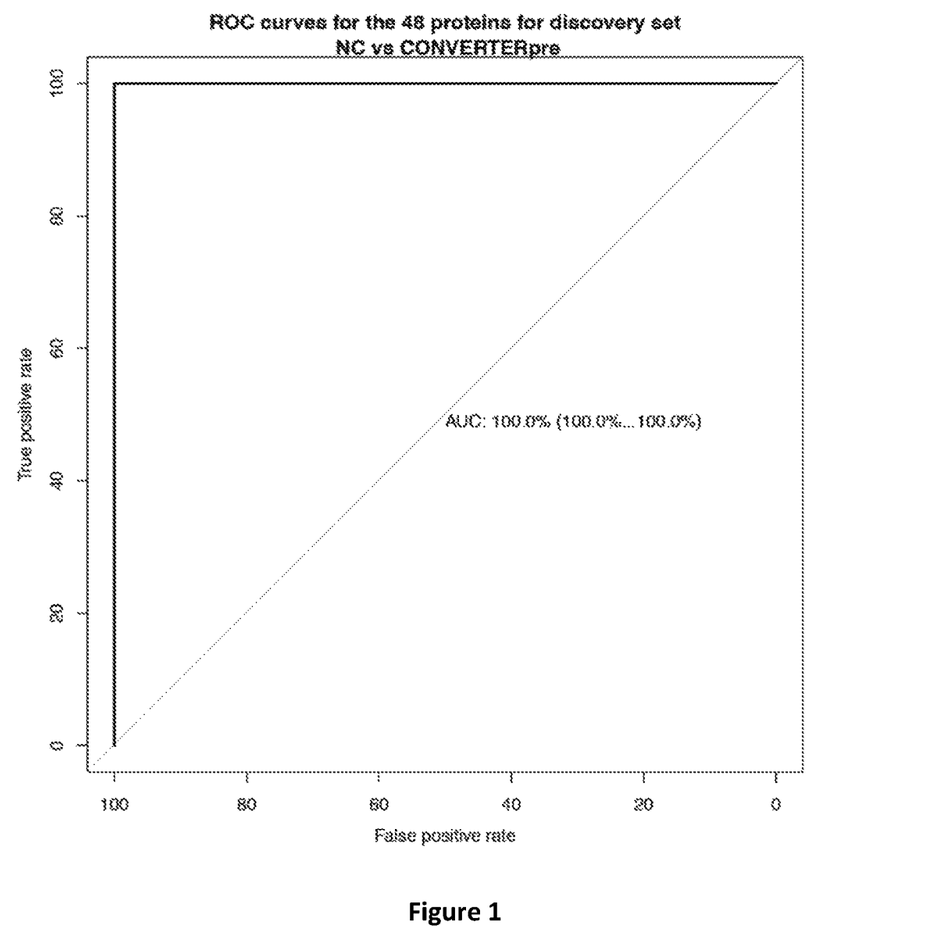
FIG. 1 depicts Receiver Operator Curves (ROC) for a set of 48 proteins involved in the predictive proteomic profile.
Figure 2:
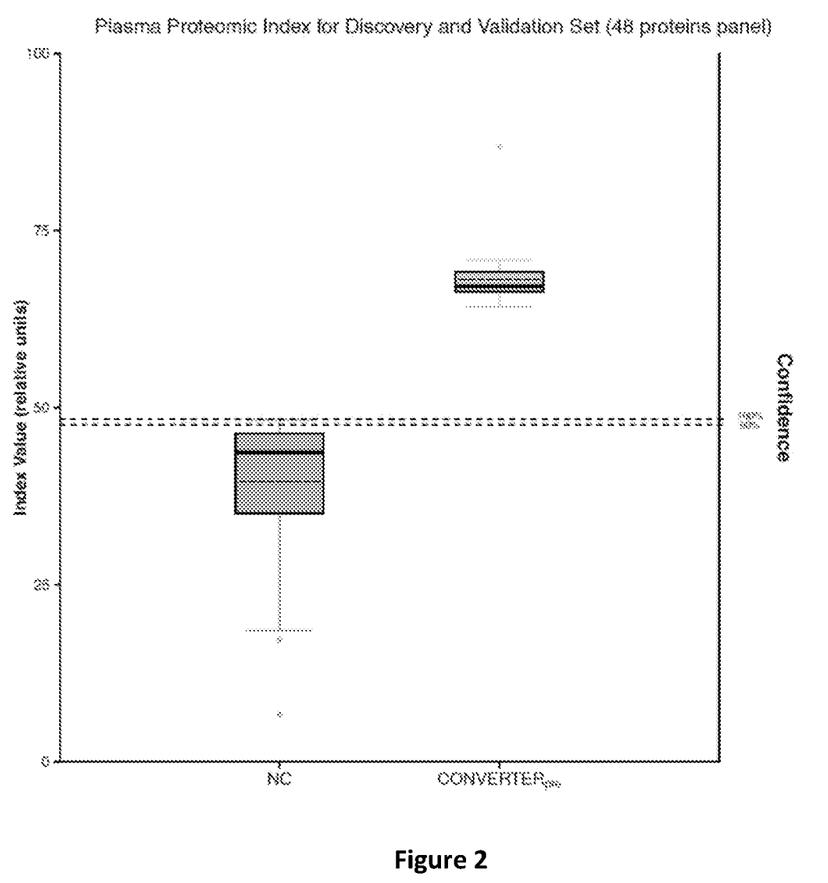

The present invention relates to methods of determining if a subject has an increased risk of suffering from memory impairment. The methods comprise analyzing at least one plasma sample from the subject to determine a value of the subject's proteomic profile and comparing the value of the subject's proteomic profile with the value of a normal proteomic profile. A change in the value of the subject's proteomic profile, over or under normal values is indicative that the subject has an increased risk of suffering from memory impairment compared to a normal individual.

As used herein, the term subject or "test subject" indicates a mammal, in particular a human or non-human primate. The test subject may or may not be in need of an assessment of a predisposition to memory impairment. For example, the test subject may have a condition or may have been exposed to injuries or conditions that are associated with memory impairment prior to applying the methods of the present invention. In another embodiment, the test subject has not been identified as a subject that may have a condition or may have been exposed to injuries or conditions that are associated with memory impairment prior to applying the methods of the present invention.

As used herein, the phrase "memory impairment" means a measureable or perceivable decline or decrease in the subject's ability to recall past events. As used herein, the term "past events" includes both recent (new) events (short-term memory) or events further back in time (long-term memory). In one embodiment, the methods are used to assess an increased risk of short-term memory impairment. In another embodiment, the methods are used to assess an increased risk in long-term memory impairment. The memory impairment can be age-related memory impairment. The memory impairment may also be disease-related memory impairment. Examples of disease-related memory impairment include but are not limited to Alzheimer's Disease, Parkinson's Disease, Multiple Sclerosis, Huntington's Disease, Pick's Disease, Progressive Supranuclear Palsy, Brain Tumor(s), Head Trauma, and Lyme Disease to name a few. In one embodiment, the memory impairment is related to amnestic mild cognitive impairment (aMCI). In another embodiment, the memory impairment is related to Alzheimer's Disease. The root cause of the memory impairment is not necessarily critical to the methods of the present invention. The measureable or perceivable decline in the subject's ability to recall past events may be assessed clinically by a health care provider, such as a physician, physician's assistant, nurse, nurse practitioner, psychologist, psychiatrist, hospice provider, or any other provider that can assess a subject's memory. The measureable or perceivable decline in the subject's ability to recall past events may be assessed in a less formal, non-clinical manner, including but not limited to the subject himself or herself, acquaintances of the subject, employers of the subject and the like. The invention is not limited to a specific manner in which the subject's ability to recall past events is assessed. In fact, the methods of the invention can be implemented without the need to assess a subject's ability to recall past events. Of course, the methods of the present invention may also include assessing the subject's ability to assess past events one or more times, both before determining the subject's proteomic profile after determining the subject's proteomic profile at least one time.

In one embodiment, the decline or decrease in the ability to recall past events is relative to each individual's ability to recall past events prior to the diagnosed decrease or decline in the ability to recall past events. In another embodiment, the decline or decrease in the ability to recall past events is relative to a population's (general, specific or stratified) ability to recall past events prior to the diagnosed decrease or decline in the ability to recall past events.

As used herein, the term means "increased risk" is used to mean that the test subject has an increased chance of developing or acquiring memory impairment compared to a normal individual. The increased risk may be relative or absolute and may be expressed qualitatively or quantitatively. For example, an increased risk may be expressed as simply determining the subject's proteomic profile and placing the patient in an "increased risk" category, based upon previous population studies. Alternatively, a numerical expression of the subject's increased risk may be determined based upon the proteomic profile. As used herein, examples of expressions of an increased risk include but are not limited to, odds, probability, odds ratio, p-values, attributable risk, relative frequency, positive predictive value, negative predictive value, and relative risk.

For example, the correlation between a subject's proteomic profile and the likelihood of suffering from memory impairment may be measured by an odds ratio (OR) and by the relative risk (RR). If $P(R^+)$ is the probability of developing memory impairment for individuals with the risk profile (R) and $P(R^-)$ is the probability of developing memory impairment for individuals without the risk profile, then the relative risk is the ratio of the two probabilities: $RR=P(R^+)/P(R^-)$.

In case-control studies, however, direct measures of the relative risk often cannot be obtained because of sampling design. The odds ratio allows for an approximation of the relative risk for low-incidence diseases and can be calculated: $OR=(F^+/(1-F^+))/(F^-/(1-F^-))$, where $F^+$ is the frequency of a risk profile in cases studies and $F^-$ is the frequency of risk profile in controls. $F^+$ and $F^-$ can be calculated using the proteomic profile frequencies of the study.

The attributable risk (AR) can also be used to express an increased risk. The AR describes the proportion of individuals in a population exhibiting memory impairment due to a specific member of the proteomic risk profile. AR may also be important in quantifying the role of individual components (specific member) in disease etiology and in terms of the public health impact of the individual marker. The public health relevance of the AR measurement lies in estimating the proportion of cases of memory impairment in the population that could be prevented if the profile or individual component were absent. AR may be determined as follows: $AR=P_E(RR-1)/(P_E(RR-1)+1)$, where AR is the risk attributable to a profile or individual component of the profile, and $P_E$ is the frequency of exposure to a profile or individual component of the profile within the population at large. RR is the relative risk, which can be approximated with the odds ratio when the profile or individual component of the profile under study has a relatively low incidence in the general population.

In one embodiment, the increased risk of a patient can be determined from p-values that are derived from association studies. Specifically, associations with specific profiles can be performed using regression analysis by regressing the proteomic profile with memory impairment. In addition, the regression may or may not be corrected or adjusted for one or more factors. The factors for which the analyses may be adjusted include, but are not limited to age, sex, weight, ethnicity, geographic location, fasting state, state of pregnancy or post-pregnancy, menstrual cycle, general health of the subject, alcohol or drug consumption, caffeine or nicotine intake and circadian rhythms, and the subject's apolipoprotein E (ApoE) genotype to name a few.

Increased risk can also be determined from p-values that are derived using logistic regression. Binomial (or binary) logistic regression is a form of regression which is used when the dependent is a dichotomy and the independents are of any type. Logistic regression can be used to predict a dependent variable on the basis of continuous and/or categorical independents and to determine the percent of variance in the dependent variable explained by the independents; to rank the relative importance of independents; to assess interaction effects; and to understand the impact of covariate control variables. Logistic regression applies maximum likelihood estimation after transforming the dependent into a "logit" variable (the natural log of the odds of the dependent occurring or not). In this way, logistic regression estimates the probability of a certain event occurring. These analyses are conducted with the program SAS.

SAS ("statistical analysis software") is a general purpose package (similar to Stata and SPSS) created by Jim Goodnight and N.C. State University colleagues. Ready-to-use procedures handle a wide range of statistical analyses, including but not limited to, analysis of variance, regression, categorical data analysis, multivariate analysis, survival analysis, psychometric analysis, cluster analysis, and non-parametric analysis.

As used herein, the phrase "proteomic profile" means the combination of a subject's proteins found in the peripheral blood or portions thereof, such as but not limited to plasma or serum. The proteomic profile is a collection of measurements, such as but not limited to a quantity or concentration, for individual proteins taken from a test sample of the subject. Examples of test samples or sources of components for the proteomic profile include, but are not limited to, biological fluids, which can be tested by the methods of the present invention described herein, and include but are not limited to whole blood, such as but not limited to peripheral blood, serum, plasma, cerebrospinal fluid, urine, amniotic fluid, lymph fluids, and various external secretions of the respiratory, intestinal and genitourinary tracts, tears, saliva, milk, white blood cells, myelomas and the like. Test samples to be assayed also include but are not limited to tissue specimens including normal and abnormal tissue.

Techniques to assay levels of individual components of the proteomic profile from test samples are well known to the skilled technician, and the invention is not limited by the means by which the components are assessed. In one embodiment, levels of the individual components of the proteomic profile are assessed using mass spectrometry in conjunction with ultra-performance liquid chromatography (UPLC), high-performance liquid chromatography (HPLC), and UPLC to name a few. Other methods of assessing levels of the individual components include biological methods, such as but not limited to ELISA assays.

The assessment of the levels of the individual components of the proteomic profile can be expressed as absolute or relative values and may or may not be expressed in relation to another component, a standard an internal standard or another molecule of compound known to be in the sample. If the levels are assessed as relative to a standard or internal standard, the standard may be added to the test sample prior to, during or after sample processing.

To assess levels of the individual components of the proteomic profile, a sample is taken from the subject. The sample may or may not processed prior assaying levels of the components of the proteomic profile. For example, whole blood may be taken from an individual and the blood sample may be processed, e.g., centrifuged, to isolate plasma or serum from the blood. The sample may or may not be stored, e.g., frozen, prior to processing or analysis.

Individual components of the proteomic profile include but are not limited to those members shown in Table 1. For the purposes of the present invention the proteomic profile comprises from least two to all 48 of the proteins listed in Table 1.

TABLE 1

| Target | TargetFullName | UniProt | Entrez GeneID | Entrez Gene Symbol |
|---|---|---|---|---|
| RANTES | C-C motif chemokine 5 | P13501 | 6352 | CCL5 |
| IGFBP-2 | Insulin-like growth factor-binding protein 2 | P18065 | 3485 | IGFBP2 |
| PRL | Prolactin | P01236 | 5617 | PRL |
| Angiopoietin-2 | Angiopoietin-2 | O15123 | 285 | ANGPT2 |
| Cystatin C | Cystatin-C | P01034 | 1471 | CST3 |
| IGFBP-6 | Insulin-like growth factor-binding protein 6 | P24592 | 3489 | IGFBP6 |
| C3 | Complement C3 | P01024 | 718 | C3 |
| kallikrein 8 | Kallikrein-8 | O60259 | 11202 | KLK8 |
| PAI-1 | Plasminogen activator inhibitor 1 | P05121 | 5054 | SERPINE1 |
| Apo E3 | Apolipoprotein E (isoform E3) | P02649 | 348 | APOE |
| DAN | Neuroblastoma suppressor of tumorigenicity 1 | P41271 | 4681 | NBL1 |
| MMP-8 | Neutrophil collagenase | P22894 | 4317 | MMP8 |
| EDAR | Tumor necrosis factor receptor superfamily member EDAR | Q9UNE0 | 10913 | EDAR |
| GFAP | Glial fibrillary acidic protein | P14136 | 2670 | GFAP |
| MIP-1a | C-C motif chemokine 3 | P10147 | 6348 | CCL3 |
| PARC | C-C motif chemokine 18 | P55774 | 6362 | CCL18 |
| Trypsin | Trypsin-1 | P07477 | 5644 | PRSS1 |
| Cathepsin D | Cathepsin D | P07339 | 1509 | CTSD |
| FCG2A/B | Low affinity immunoglobulin gamma Fc region receptor II-a/b | P12318 P31994 | null | FCGR2A FCGR2B |
| CAMK1D | Calcium/calmodulin-dependent protein kinase type 1D | Q8IU85 | 57118 | CAMK1D |
| b2-Microglobulin | Beta-2-microglobulin | P61769 | 567 | B2M |
| GCP-2 | C-X-C motif chemokine 6 | P80162 | 6372 | CXCL6 |
| HGFA | Hepatocyte growth factor activator | Q04756 | 3083 | HGFAC |
| p27Kip1 | Cyclin-dependent kinase inhibitor 1B | P46527 | 1027 | CDKN1B |

TABLE 1-continued

| Target | TargetFullName | UniProt | Entrez GeneID | Entrez Gene Symbol |
|---|---|---|---|---|
| ANGL4 | Angiopoietin-related protein 4 | Q9BY76 | 51129 | ANGPTL4 |
| PPAC | Low molecular weight phosphotyrosine protein phosphatase | P24666 | 52 | ACP1 |
| PSA6 | Proteasome subunit alpha type-6 | P60900 | 5687 | PSMA6 |
| MED-1 | Mediator of RNA polymerase II transcription subunit 1 | Q15648 | 5469 | MED1 |
| 6-Phosphogluconate dehydrogenase | 6-phosphogluconate dehydrogenase, decarboxylating | P52209 | 5226 | PGD |
| M2-PK | Pyruvate kinase PKM | P14618 | 5315 | PKM2 |
| CRP | C-reactive protein | P02741 | 1401 | CRP |
| MSP | Hepatocyte growth factor-like protein | P26927 | 4485 | MST1 |
| TGM3 | Protein-glutamine gamma-glutamyltransferase E | Q08188 | 7053 | TGM3 |
| TNF-b | Lymphotoxin-alpha | P01374 | 4049 | LTA |
| 41 | Protein 4.1 | P11171 | 2035 | EPB41 |
| IL-3 | Interleukin-3 | P08700 | 3562 | IL3 |
| ITI heavy chain H4 | Inter-alpha-trypsin inhibitor heavy chain H4 | Q14624 | 3700 | ITIH4 |
| IL-1a | Interleukin-1 alpha | P01583 | 3552 | IL1A |
| MCP-3 | C-C motif chemokine 7 | P80098 | 6354 | CCL7 |
| WNT7A | Protein Wnt-7a | O00755 | 7476 | WNT7A |
| Peroxiredoxin-5 | Peroxiredoxin-5, mitochondrial | P30044 | 25824 | PRDX5 |
| PGP9.5 | Ubiquitin carboxyl-terminal hydrolase isozyme L1 | P09936 | 7345 | UCHL1 |
| SIRT2 | NAD-dependent protein deacetylase sirtuin-2 | Q8IXJ6 | 22933 | SIRT2 |
| IL-17B R | interleukin-17 receptor B | Q9NRM6 | 55540 | IL17RB |
| NKp46 | Natural cytotoxicity triggering receptor 1 | O76036 | 9437 | NCR1 |
| SIG14 | Sialic acid-binding Ig-like lectin 14 | Q08ET2 | 100049587 | SIGLEC14 |
| calreticulin | Calreticulin | P27797 | 811 | CALR |
| sLeptin R | Leptin receptor | P48357 | 3953 | LEPR |

In one embodiment, the individual levels of each of the proteins are lower than those compared to normal levels. In another embodiment, the individual levels of each of the proteins are lower than those compared to normal levels. In another embodiment, the individual levels of some of the proteins are lower than those compared to normal levels.

The levels of depletion or augmentation of the proteins compared to normal levels can vary. In one embodiment, the levels of any one or more of the proteins is at least 1.05, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20 lower than normal levels. In another embodiment, the levels of any one or more of the proteins is at least 1.05, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20 higher than normal levels. For the purposes of the present invention, the number of "times" the levels of a protein is lower or higher over normal can be a relative or absolute number of times. In the alternative, the levels of the proteins may be normalized to a standard and these normalized levels can then be compared to one another to determine if a protein is lower or higher.

The subject's proteomic profile is compared to the profile that is deemed to be a normal proteomic profile. To establish the proteomic profile of a normal individual, an individual or group of individuals may be first assessed for their ability to recall past events to establish that the individual or group of individuals has a normal or acceptable ability memory. Once established, the proteomic profile of the individual or group of individuals can then be determined to establish a "normal proteomic profile." In one embodiment, a normal proteomic profile can be ascertained from the same subject when the subject is deemed to possess normal cognitive abilities and no signs (clinical or otherwise) of memory impairment. In one embodiment, a "normal" proteomic profile is assessed in the same subject from whom the sample is taken prior to the onset of measureable, perceivable or diagnosed memory impairment. That is, the term "normal" with respect to a proteomic profile can be used to mean the subject's baseline proteomic profile prior to the onset of memory impairment. The proteomic profile can then be reassessed periodically and compared to the subject's baseline proteomic profile. Thus, the present invention also include methods of monitoring the progression of memory impairment in a subject, with the methods comprising determining the subject's proteomic profile more than once over a period of time. For example, some embodiments of the methods of the present invention will comprise determining the subject's proteomic profile two, three, four, five, six, seven, eight, nine, 10 or even more times over a period of time, such as a year, two years, three, years, four years, five years, six years, seven years, eight years, nine years or even 10 years or longer. The methods of monitoring a subject's risk of having memory impairment would also include embodiments in which the subject's proteomic profile is assessed during and after treatment of memory impairment. In other words, the present invention also includes methods of monitoring the efficacy of treatment of proteomic impairment by assessing the subject's proteomic profile over the course of the treatment and after the treatment. The treatment may be any treatment designed to increase a subject's ability to recall past events, i.e., improve a subject's memory.

In another embodiment, a normal proteomic profile is assessed in a sample from a different subject or patient (from the subject being analyzed) and this different subject does not have or is not suspected of having memory impairment. In still another embodiment, the normal proteomic profile is assessed in a population of healthy individuals, the constituents of which display no memory impairment. Thus, the subject's proteomic profile can be compared to a normal proteomic profile generated from a single normal sample or a proteomic profile generated from more than one normal sample.

Of course, measurements of the individual components, e.g., concentration, of the normal proteomic profile can fall within a range of values, and values that do not fall within this "normal range" are said to be outside the normal range. These measurements may or may not be converted to a value, number, factor or score as compared to measurements in the "normal range." For example, a measurement for a specific protein that is below the normal range, may be assigned a value or −1, −2, −3, etc., depending on the scoring system devised.

In one embodiment, the "proteomic profile value" can be a single value, number, factor or score given as an overall collective value to the individual molecular components of the profile. For example, if each component is assigned a value, such as above, the proteomic value may simply be the overall score of each individual value. For example, if 10 of the components of the proteomic profile are used to create the profile value, and five of the components are assigned values of "−2" and five are assigned values of "−1," the proteomic profile in this example would be −15, with a normal value being, for example, "0." In this manner, the proteomic profile value could be useful single number or score, the actual value or magnitude of which could be an indication of the actual risk of memory impairment, e.g., the "more negative" the value, the greater the risk of memory impairment.

In another embodiment the "proteomic profile value" can be a series of values, numbers, factors or scores given to the individual components of the overall profile. In another embodiment, the "proteomic profile value" may be a combination of values, numbers, factors or scores given to individual components of the profile as well as values, numbers, factors or scores collectively given to a group of components. In another example, the proteomic profile value may comprise or consist of individual values, number, factors or scores for specific component as well as values, numbers, factors or scores for a group on components.

In another embodiment individual values from the proteins can be used to develop a single score, such as a "combined proteomic index," which may utilize weighted scores from the individual component values reduced to a diagnostic number value. The combined proteomic index may also be generated using non-weighted scores from the individual component values. When the "combined proteomic index" exceeds (or is less than) a specific threshold level, the individual has a high risk of memory impairment, whereas the maintaining a normal range value of the "combined proteomic index" would indicate a low or minimal risk of memory impairment. In this embodiment, the threshold value would be set by the combined proteomic index from normal subjects.

In another embodiment, the value of the proteomic profile can be the collection of data from the individual measurements and need not be converted to a scoring system, such that the "proteomic profile value" is a collection of the individual measurements of the individual components of the profile.

If it is determined that a subject has an increased risk of memory impairment, the attending health care provider may subsequently prescribe or institute a treatment program. In this manner, the present invention also provides for methods of screening individuals as candidates for treatment of memory impairment. The attending healthcare worker may begin treatment, based on the subject's proteomic profile, before there are perceivable, noticeable or measurable signs of memory impairment in the individual.

Similarly, the invention provides methods of monitoring the effectiveness of a treatment for memory impairment. Once a treatment regimen has been established, with or without the use of the methods of the present invention to assist in a diagnosis of memory impairment, the methods of monitoring a subject's proteomic profile over time can be used to assess the effectiveness of a memory impairment treatment. Specifically, the subject's proteomic profile can be assessed over time, including before, during and after treatments for memory impairment. The proteomic profile can be monitored, with, for example, a decline in the values of the profile over time being indicative that the treatment may not be as effective as desired.

All patents and publications mentioned in this specification are indicative of the level of those skilled in the art to which the invention pertains. All patents and publications cited herein are incorporated by reference to the same extent as if each individual publication was specifically and individually indicated as having been incorporated by reference in its entirety

EXAMPLES

Example 1

Neurocognitive Methods

A total of 525 volunteers participated in this study as part of the Rochester/Orange County Aging Study (R/OCAS), an ongoing natural history study of cognition in community-dwelling older adults. Briefly, participants were followed with yearly cognitive assessments and blood samples were collected following an overnight fast and withholding of all medications. At baseline and each yearly visit, participants completed assessments in such as activities in daily living, memory complaints, signs and symptoms of depression, and were administered a detailed cognitive assessment.

For this study, data from the cognitive tests were used to classify participants into groups for biomarker discovery. Standardized scores (Z-scores) were derived for each participant on each cognitive test and the composite Z-scores were computed for five cognitive domains (attention, executive, language, memory, visuoperceptual) (Table 2).

TABLE 2

| Attention ($Z_{att}$) | Executive ($Z_{exe}$) | Language ($Z_{lan}$) | Visuoperceptual ($Z_{vis}$) | Memory ($Z_{mem}$) |
|---|---|---|---|---|
| Wechsler Memory Scale-III Forward Digit Span (WMS-III FDS) | Wechsler Memory Scale-III Backward Digit Span (WMS-III BDS) | 1-min Category fluency (Animals) | Hooper Visual Organization Test (HVOT) | Rey Auditory Verbal Learning Test Learning (RAVLT Learning) |
| Trail Making Test- Part A (TMT-A) | Trail Making Test- Part B (TMT-B) | Boston Naming Test 60-Item version (BNT-60) | | Rey Auditory Verbal Learning Test Retrieval (RAVLT Retrieval) Rey Auditory Verbal Learning Test Retention (RAVLT Recognition) |

Normative data for Z-score calculations were derived from the performance of the participants on each of the cognitive tests adjusted for age, education, sex, and visit. To reduce the effect of cognitively impaired participants on the mean and SD, age-, education-, sex, and visit-adjusted residuals from each domain Z-score model were robustly standardized to have median 0 and robust SD=1, where the robust SD=IQR/1.35, as 1.35 is the IQR (Inter-Quartile Range) of a standard normal distribution.

The participants were then categorized into groups of incident aMCI or early AD (combined into one category aMCI/AD), cognitively normal control (NC), and those who converted to MCI or AD over the course of the study (Converters) based on these composite scores. Impairment was defined as a Z-score 1.35 SD below the cohort median. All participants classified as aMCI met recently revised criteria for the amnestic subtype of MCI. Other behavioral phenotypes of MCI were excluded to concentrate on the amnestic form, which most likely represents nascent Alzheimer's pathology. All early AD participants met recently revised criteria for probable Alzheimer's disease with impairment in memory and at least one other cognitive domain. For the MCI and early AD groups, scores on the measures of memory complaints (MMQ) and activities of daily living (PGC-IADL) were used to corroborate research definitions of these states. All Converters had non-impaired memory at entry to the study ($Z_{mem} \geq -1.35$), developed memory impairment over the course of the study ($Z_{mem} \leq -1.35$) and met criteria for the above definitions of aMCI or AD. To enhance the specificity of the biomarker analyses, NC participants in this study were conservatively defined with $Z_{mem} \pm 1$ SD of the cohort median rather than simply $\geq -1.35$, and all other Z-scores $\geq -1.35$ SD.

For each subject, $Z_{mem}$(last), $Z_{att}$(last), $Z_{exe}$(last), $Z_{lan}$(last), and $Z_{vis}$(last) were defined as the age-gender-education-visit-adjusted robust Z-scores for the last available visit for each subject. The aMCI/AD group was defined as those participants whose adjusted $Z_{mem}$ was 1 IQR below the median at their last available visit, i.e., $Z_{mem}$(last)$\leq -1.35$. Converters were defined as that subset of the a MCI/AD group whose adjusted $Z_{mem}$ at baseline visit 0 was no more than 1 IQR below the median, i.e., $Z_{mem}$(visit=0)>−1.35 and $Z_{mem}$(last)$\leq -1.35$. Participants were classified as NC if they had central scores on all domains at both the first and last visits, i.e., only if they met all of the following six conditions: (i) $-1 < Z_{mem}$(last)$<1$, (ii) $-1 < Z_{mem}$(visit=0)$<1$, (iii) $Z_{min}$(last)$> -1.35$, (iv) $Z_{min}$(visit=0)$> -1.35$, (v) $Z_{max}$(last) $<1.35$, and (vi) $Z_{max}$(visit=0)$<1.35$, where $Z_{max}$(last) and $Z_{max}$(visit=0) denote the maximum of the five adjusted Z-scores at the last and first visits, respectively. $Z_{mem}$ for normal participants had to be within 0.74 IQR (1 SD) of the median, rather than just 1 IQR (1.35 SD), to guarantee that they were >0.25 IQR (0.35 SD) from aMCI/AD participants.

After three years of being in the study, (December, 2010), 202 participants had completed a baseline and two yearly visits. At the third visit, 53 participants met criteria for aMCI/AD and 96 met criteria for NC. Of the 53 aMCI/AD participants, 18 were Converters and 35 were incident aMCI or AD. The remaining 53 participants did not meet the criteria for either group and were not considered for biomarker profiling. Some of these individuals met criteria for non-amnestic MCI and many had borderline or even above average memory scores that precluded their inclusion as either aMCI/AD or NC. 53 of the NC participants were matched to the 53 aMCI/AD participants based on sex, age, and education level. Blood samples were obtained on the last available study visit for the 53 MCI/AD and the 53 NC for biomarker discovery. Two blood samples from each of the 18 Converters were also included: one from the baseline visit ($C_{pre}$) when $Z_{mem}$ was non-impaired and one from the third visit ($C_{post}$) when $Z_{mem}$ was impaired and they met criteria for either aMCI or AD. Thus, at total of 124 samples from 106 participants were analyzed.

Internal cross-validation was employed to validate findings from the discovery phase. Blood samples for validation were identified at the end of the fifth year of the study and all 106 participants included in the discovery phase were excluded from consideration for the validation phase. Cognitive composite Z-scores were re-calculated based on the entire sample available and the same procedure and criteria were used to identify samples for the validation phase. A total of 145 participants met criteria for a group: 21aMCI/AD and 124 NC. Of the 21 aMCI/AD, 10 were Converters. 20 of the NC participants were matched to the aMCI/AD participants on the basis of age, sex, and education level as in the discovery phase. In total, 41 participants contributed samples to the validation phase and, as before, the 10 Converters also contributed a baseline sample ($C_{pre}$) for a total of 51 samples.

Neurocognitive Statistical Analyses

The neurocognitive analyses were designed to demonstrate the general equivalence of the discovery and validation samples on clinical and cognitive measures. Separate Multivariate Analysis of Variance (MANOVA's) tests were used to examine discovery/validation group performance on the composite Z-scores and on self-report measures of memory complaints, memory related functional impairment, depressive symptoms, and a global measure of cognitive function. In the first MANOVA, biomarker sample (discovery, validation) was the independent variable and MMQ, IADL, GDS, and MMSE were the dependent variables. In the second MANOVA, biomarker sample (discovery, validation) was the independent variable and the five cognitive domain Z-scores ($Z_{att}$, $Z_{exe}$, $Z_{lan}$, $Z_{mem}$, and $Z_{vis}$) were the dependent variables. Significance was set at alpha=0.05 and Tukey's HSD procedure was used for post-hoc comparisons. All statistical analyses were performed using SPSS (version 21).

Example 2

Protein Statistical Analyses

Once the proteins were extracted and quantified, the m/z features of proteins were normalized with log transformation that stabilized the variance followed with a quantile normalization to make the empirical distribution of intensities the same across samples. The proteins were selected among all those known to be identifiable using a ROC regularized learning technique, based on the least absolute shrinkage and selection operator (LASSO) penalty as implemented with the R package 'glmnet', which uses cyclical coordinate descent in a pathwise fashion. The regularization path over a grid of values was obtained for the tuning parameter lambda through 10-fold cross-validation. The optimal value of the tuning parameter lambda, which was obtained by the cross-validation procedure, was then used to fit the model. All the features with non-zero coefficients were retained for subsequent analysis. The classification performance of the selected proteins was assessed using area under the ROC (receiver operating characteristic) curve (AUC). The ROC can be understood as a plot of the probability of classifying correctly the positive samples against the rate of incorrectly classifying true negative samples. Thus the AUC measure of an ROC plot is actually a measure of predictive accuracy.

Results

Over the course of the study, 74 participants met criteria for either aMCI or mild AD, 46 of these were incidental cases at entry and 28 phenoconverted (Converters) from a non-impaired memory status at entry ($C_{pre}$). The average time to phenoconversion was 2.1 years (range=1-5 years). 53 aMCI/AD participants were selected, including 18 Converters, and 53 age-, education-, and sex-matched cognitively normal control (NC) participants for untargeted proteomic biomarker discovery. Internal cross validation was used to evaluate the accuracy of the discovered proteomic profile in classifying a blinded sample of 51 subjects consisting of the remaining subset of 21 aMCI/AD participants, including 10 Converters, and an additional 20 matched NC.

The aMCI/AD, Converter, and NC groups were defined primarily using a composite measure of memory performance in addition to composite measures of other cognitive abilities and clinical measures of memory complaints and functional capacities. (See Tables 2 and 3).

TABLE 3

| Clinical/Cognitive Measures | Dependent Measure (Range) | Domain Assessed |
| --- | --- | --- |
| Multiple Assessment Inventory IADL Scale (MAI-IADL) Lawton M P. (1988) Instrumental Activities of Daily Living (IADL) scale: Original observer-rated version. *Psychopharmacology Bulletin*, 24, 785-7. | Total Score (0-27) | Functional capacities |
| Multifactorial Memory Questionnaire (MMQ) Troyer A K and Rich J B. (2002). Psychometric properties of a new metamemory questionnaire for older adults. *Journal of Gerontology*, 57(1), 19-27. | Total Score (0-228) | Memory complaints |
| Mini Mental State Examination (MMSE) Folstein, M F, Folstein, S E, and McHugh, P R. (1975). "Mini-mental state". *Journal of Psychiatric Research*, 12, 189-98. | Total Score (0-30) | Global cognitive ability |
| Geriatric Depression Scale-Short Form (GDS-SF) Sheikh J I and Yesavage J A. (1986). Geriatric Depression Scale (GDS): Recent evidence and development of a shorter version. *Clinical Gerontologist*, 5, 165-173. | Total Score (0-15) | Mood |
| Wechsler Memory Scale-III Forward Digit Span (WMS-III FDS) Wechsler D. *Wechsler Memory Scale-III Manual*. San Antonio, TX: The Psychological Corporation, 1997. | Span Length (0-9) | Attention |
| Trail Making Test- Part A (TMT-A) Reitan R M. (1958). Validity of the Trail Making Test as an indicator of organic brain damage. *Perceptual and Motor Skills*, 8, 271-6. | Completion time (1-300 seconds) | Attention |
| Wechsler Memory Scale-III Backward Digit Span (WMS-III BDS) Wechsler D. *Wechsler Memory Scale-III Manual*. San Antonio, TX: The Psychological Corporation, 1997. | Span Length (0-8) | Executive ability |
| Trail Making Test- Part B (TMT-B) Reitan R M. (1958). Validity of the Trail Making Test as an indicator of organic brain damage. *Perceptual and Motor Skills*, 8, 271-6. | Completion Time (1-300 seconds) | Executive ability |
| Category fluency (Animals) Borkowski J, Benton A, Spreen O. (1967). Word fluency and brain damage. *Neuropsychologia*, 5, 135-140 | Animals named in 1-minute | Language |
| Boston Naming Test 60-Item version (BNT-60) Kaplan E, Goodglass H, and Weintraub S. (1983). Boston Naming Test. Philadelphia: Lea & Feibiger. | Total Correct (0-60) | Language |
| Rey Auditory Verbal Learning Test Learning (RAVLT Learning) | Total words recalled over Trials | Verbal learning |

TABLE 3-continued

| Clinical/Cognitive Measures | Dependent Measure (Range) | Domain Assessed |
|---|---|---|
| Rey A. (1964). L'examen clinique en psychologie. Paris: Presses Universitaires de France. | 1-5 (0-75) | |
| Rey Auditory Verbal Learning Test Recall (RAVLT Retrieval) | Words recalled at 20-minute delay | Verbal retrieval |
| Rey A. (1964). L'examen clinique en psychologie. Paris: Presses Universitaires de France. | (0-15) | |
| Rey Auditory Verbal Learning Test Retention (RAVLT Recognition) | True positives - false positives | Verbal retention |
| Rey A. (1964). L'examen clinique en psychologie. Paris: Presses Universitaires de France. | (0-15) | |
| Hooper Visual Organization Test (HVOT) | Total score | Visuoperception |
| Hooper H E. Hooper Visual Organization Test (VOT) Los Angeles: Western Psychological Services; 1983. | (0-30) | |

To confirm the reproducibility of the protein panel from the discovery samples, targeted quantitative proteomics analyses was performed using plasma from the independent validation group of all specimens used as an independent cross validation. One sample from the MCI/AD group was not available for proteomic analysis. The validation samples were obtained from the last available visit from the aMCI/AD, $C_{pre}$, and NC groups and were designated as groups A, B, and C and analyzed in a blinded fashion, without specification of diagnostic identities. The samples were processed and analyzed using the same techniques as in the discovery phase. The blinded data were statistically analyzed to determine if the unknown groups could be characterized into the correct diagnostic categories based solely on the levels of the proteomic panel.

The proteomic data was used from the untargeted LASSO analysis to build separate linear classifier models that would distinguish the $C_{pre}$ group from the NC group. A receiver operating characteristic (ROC) analysis was employed to determine the area under the ROC curve (AUC) to assess the performance of the classifier models in differentiating the groups. When distinguishing between the $C_{pre}$ and NC groups, the LASSO identified proteins yielded an AUC of 0.983. These high AUC values demonstrate robust discrimination between the $C_{pre}$ and NC groups by the models. Using the same linear classifier method, a simple logistic model was constructed using just the protein panel and used this to classify the same groups.

What is claimed is:

1. A method of treating a subject who has an increased risk of suffering from memory impairment, the method comprising
   a) determining if a subject has an increased risk of suffering from memory impairment by analyzing at least one sample from the subject to determine the level of proteins in the subject's proteomic profile, and comparing the level of proteins in the subject's proteomic profile with the level of proteins obtained from subjects determined to define a normal proteomic profile; and
   b) administering a treatment for memory impairment to the subject when the level of proteins in the subject's proteomic profile is lower compared to the level of proteins in the normal proteomic profile,
   wherein a lower level of proteins in the subject's proteomic profile is indicative that the subject has an increased risk of suffering from future memory impairment compared to those defined as having a normal proteomic profile, and
   wherein the proteomic profile comprises C-C motif chemokine 5; insulin-like growth factor binding protein 2; prolactin; angiopoietin-2; cystatin C; insulin-like growth factor-binding protein 6; complement C3; kallikrein-8; plasminogen activator inhibitor 1; apolipoprotein E (isoform E3); neuroblastoma suppressor of tumorigenicity 1; neutrophil collagenase; tumor necrosis factor receptor superfamily member EDAR; glial fibrillary acidic protein; C-C motif chemokine 3; C-C motif chemokine 18; trypsin-1; cathepsin D; low affinity immunoglobulin gamma Fc region receptor II a/b; calcium/calmodulin-dependent protein kinase type 1D; beta-2-microglobulin; C-X-C motif chemokine 6; hepatocyte growth factor activator; cyclin-dependent kinase inhibitor 1B; angiopoietin-related protein 4; low molecular weight phosphotyrosine protein phosphatase; proteasome subunit alpha type-6; mediator of RNA polymerase II transcription subunit 1; 6-phosphogluconate dehydrogenase, decarboxylating; pyruvate kinase PKM; C-reactive protein; hepatocyte growth factor-like protein; protein-glutamine gamma-glutamyltransferase E; lymphotoxin-alpha; protein 4.1; interleukin-3; inter-alpha-trypsin inhibitor heavy chain H4; interleukin-1 alpha; C-C motif chemokine 7; protein Wnt-7a; peroxiredoxin-5, mitochondrial; ubiquitin carboxyl-terminal hydrolase isozyme L1; NAD-dependent protein deacetylase sirtuin-2; interleukin-17 receptor B; natural cytotoxicity triggering receptor 1; sialic acid-binding Ig-like lectin 14; calreticulin; and leptin receptor.

2. The method of claim 1, wherein the normal proteomic profile comprises the subject's proteomic profile prior to the onset of memory impairment.

3. The method of claim 1, wherein the normal proteomic profile comprises a proteomic profile generated from a population of individuals that do not presently or in the future display memory impairment.

* * * * *